United States Patent [19]

Russell

[11] 4,058,438

[45] Nov. 15, 1977

[54] RAPID UNIVERSAL SENSING CELL

[75] Inventor: William J. Russell, Sparta, N.J.

[73] Assignee: The United States of America as represented by the Secretary of the Army, Washington, D.C.

[21] Appl. No.: 736,614

[22] Filed: Oct. 28, 1976

Related U.S. Application Data

[63] Continuation-in-part of Ser. No. 597,059, July 18, 1975, abandoned.

[51] Int. Cl.² .................. G01N 27/00; C25F 3/00; G01N 27/26
[52] U.S. Cl. .................. 204/1 T; 204/129.2; 204/195 R
[58] Field of Search .......... 204/129.2, 1 T, 195 R; 156/627, 345

[56] References Cited

U.S. PATENT DOCUMENTS

| 3,375,178 | 3/1968 | Locke | 204/1 T |
| 3,438,875 | 4/1969 | Watanabe et al. | 204/195 F X |
| 3,874,959 | 4/1975 | Hoekstra et al. | 204/129.2 X |

Primary Examiner—Anthony Skapars
Assistant Examiner—D. R. Valentine
Attorney, Agent, or Firm—Nathan Edelberg; A. Victor Erkkila; Max Yarmovsky

[57] ABSTRACT

An electrolytic cell which comprises a standard calomel electrode supported in a container containing an etchant and a sample of the alloy or metal to be etched are electrically connected to a millivoltmeter or an X-Y recorder. The variation in potential generated by the electrolytic cell is measured as a function of time and used to determine the optimum time at which to end the process.

2 Claims, 1 Drawing Figure

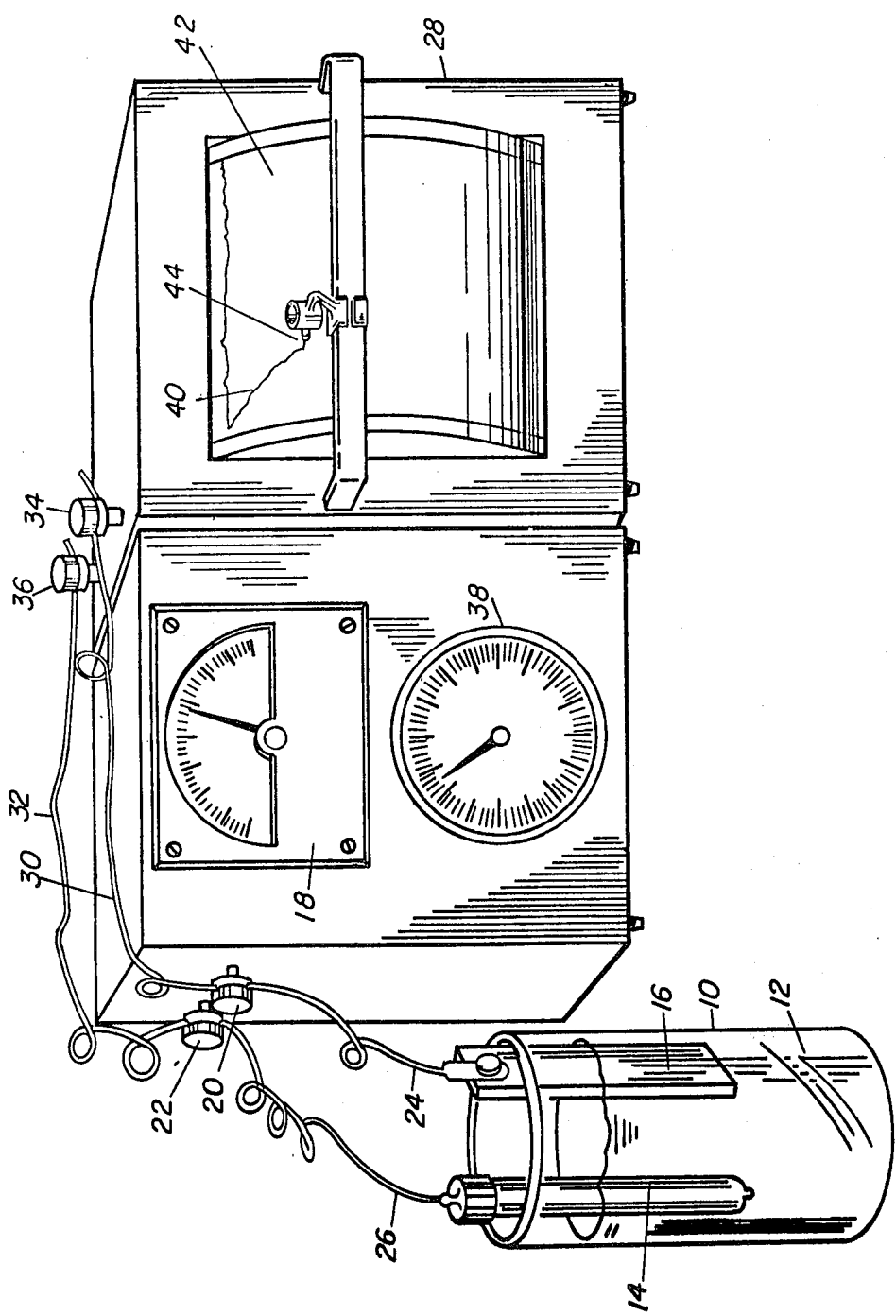

RAPID UNIVERSAL SENSING CELL

GOVERNMENTAL INTEREST

The invention described herein may be manufactured, used and licensed by or for the Government for governmental purposes without the payment to me of any royalties thereon.

This application is a continuation-in-part of a prior application Ser. No. 597,059 filed on July 18, 1975 now abandoned of William J. Russell for a Rapid Universal Sensing Cell.

BACKGROUND OF THE INVENTION

Various means were used in the prior art to determine when a metal surface should be removed from an etchant solution so that it would be properly prepared for resistance welding and or adhesive bonding. In the past, the time that a material was to be etched was empirically determined by evaluating a test cupon after it had been exposed to the etchant for a specific internal time. The suitability of the particular time chosen for the test specimen to remain in the etchant was generally evaluated by resistance welding and or adhesively bonding representative cupons, and then destructively testing them to select a processing condition that gave the most desirous test characteristics.

Frequently, the prior art test devices and methods were unsatisfactory because relatively large quantities of material could be processed before a deficiency was detected. The lack of a rapid sensing cell to monitor the process often resulted in the production of material which produced weak bonds. The need to inspect and remove such defective material from an assembly line generally resulted in waste of material, time and labor.

SUMMARY OF THE INVENTION

The present invention relates to a device and process for determining the optimum point for halting the surface treating of a metal material being prepared for resistance welding and/or adhesive bonding. The present invention utilizes an electro-chemical cell which comprises a sample of the metal to be surface treated or etched as one electrode of the cell, an etchant material which also serves as an electrolyte, a standard calomel electrode half cell as a reference electrode, and a means for measuring the rate of change of voltage, generated in the electro-chemical cell, as a function of time.

An object of the present invention is to provide a universal sensing cell for non-destructively monitoring the reaction of a metal surface with a chemical processing solution.

Another object of the present invention is to provide a universal sensing cell to immediately detect the occurrence of undesirable processing variations in a surface treatment or etching process.

A further object of the present invention is to provide a universal cell for a material being etched which measures when the curve produced by plotting electrode potential as a function of time approaches a constant.

For a better understanding of the present invention, together with other and further objects thereof, reference is made to the following descriptions taken in connection with the accompanying drawings.

BRIEF DESCRIPTION OF THE DRAWINGS

The FIGURE is an isometric view of an electrochemical cell, a combination clock and potentiometer electrically connected to the cell and an X-Y recording instrument electrically connected in parallel with the potentiometer and cell.

DETAILED DESCRIPTION OF THE PREFERRED EMBODIMENTS

Referring now to the FIGURE a container 10 holds an etchant 12 therein and a standard calomel electrode 14 and a sample 16 of the alloy to be etched. A sensitive millivoltmeter 18 is electrically connected to the reference electrode 14 and the piece of metal 16 to be etched at its input terminals 20 and 22 by electrical conductors 24 and 26 respectively. An X-Y recorder 28 may be substituted for the millivoltmeter 18 or may be electrically connected in parallel therewith by electrical conductors 30 and 32 at the X-Y recorder input terminals 34 and 36 respectively. A timer 38 is provided to measure the elapsed etching time.

In operation when the reference electrode 14 and a piece of metal 16 are electrically connected to the potentiometer 18 and/or the X-Y recorder 28, and the electrodes 14 and 16 are immersed into the etchant-electrolyte 12, an electrical potential is generated which may be measured as a function of time by X-Y recorder 28 and automatically plotted as shown by curve 40 on recorder paper 42. The potential being measured across the millivoltmeter input terminals 20 and 22 and the X-Y recorder input terminals 34 and 36 is that which is produced by the etchant-electrolyte bath 12 in combination with the standard half cell 14 and the material 16 being etched. In like manner, curve 40 may be plotted by hand by the operator on the basis of periodic voltage readings taken on potentiometer 18 and time readings on timer 38. The potential when plotted as a function of time will give a curve which is repeatable and characteristic of the etchant-electrolyte and alloy used. It has been empirically determined that the best surface for resistance welding and/or adhesive bonding is obtained when the curve produced by plotting electrode potential with time approaches and/or stabilizes at a constant potential such as exhibited by point 44 on curve 40. Unexpected change in the shape of the plotted potential versus time curve generally indicate unwanted and undesirable changes in the process. This change in the shape of the curve signals the need for corrective action to prevent the improper surface treatment of the metal being etched. Etchant-electrolyte materials which provide suitable etchant-electrolyte properties are Amchem #4 and Amchem #17, Deoxidizer, as manufactured by Amchem Products, Inc. of Ambler, Pa; Clepo 180S, Deoxidizer, as manufactured by Fredrick Gumm Chemical Co., Inc. of Kearny, NJ; or a solution consisting of the following:

$33\frac{1}{2}$ grams of $Na_2Cr_2O_7 \cdot 5\ H_2O$ 181 ml concentrated $H_2SO_3$ diluted to 1 liter with deionized water and used at 140°–160° F.

A suitable method of carrying out the etching of an aluminum metal member would include the steps of connecting the metal sample 16 to be etched to a terminal 20 of a potentiometer 18; then connecting a reference electrode 14 made of such material as calomel, to the other terminal 22 of the potentiometer 18; immersing the metal member 16 and the reference electrode 14 in a container 12 which contains an etchant-electrolyte 12, deoxidizing chemical solution, such as Amchem #4 or Amchem #17, or Clepo 180S; observing the potential generated by the electro-chemical cell aforedescribed over a period of time in order to determine when the potential being measured approaches a stabilized value; metal member 16 being etched is then removed from the etchant-electrolyte bath 12 when the potential shown by the potentiometer 18 or being drawn by the X-Y recorder 28 approaches a steady value, as illustrated by point 44 on curve 40; and then rinsing the metal member 16 with water to remove any residual etchant 12 therefrom.

The foregoing disclosure and drawing is merely illustrative of the principles of this invention and are not to be interpreted in a limiting sense. I wish it to be understood that I do not desire to be limited to the exact details of construction shown and process described for obvious modifications will occur to a person skilled in the art.

Having thus fully described the invention, what is claimed as new and desired to be secured by Letters Patent of the United States is:

1. A method for determining etching time for preparing a consistent metal surface for resistance welding and adhesive bonding which comprises:

electrically coupling a standard half cell and a sample of the material to be etched to the terminals of a potentiometer;

placing the sample to be etched in an etchant-electrolyte bath;

placing a standard half cell in said bath;

monitoring the potential being produced by said etchant-electrolyte bath in combination with said standard half cell and the sample being etched;

recording the elasped time at which the potential measured by said potentiometer approaches a steady value.

2. A method as recited in claim 1 wherein the preparation of said etchant-electrolyte bath includes:

weighing out 33½ grams of $Na_2Cr_2O_7 \cdot 5 H_2O$;

measuring out 181 ml of concentrated $H_2SO_4$;

diluting said 181 ml concentrated $H_2SO_4$ with 1 liter of deionized water to form a diluted $H_2SO_4$ solution;

mixing together said 33½ grams of $Na_2Cr_2O_7 \cdot 5 H_2O$ with said diluted $H_2SO_4$ solution;

placing said etchant-electrolyte bath in a container large enough to hold said material to be etched and standard half cell; and heating said etchant-electrolyte bath to a temperature within the range of 140°–160° F.

* * * * *